United States Patent [19]

Humphries et al.

[11] 4,426,879
[45] Jan. 24, 1984

[54] METHOD AND APPARATUS FOR DETERMINING THE FOAMING CHARACTERISTICS OF CRUDE OIL

[75] Inventors: Curtis L. Humphries, Duncanville; Eddie F. Schultz, Arlington; Alan M. Winkelman, Dallas, all of Tex.

[73] Assignee: Mobil Oil Corporation, New York, N.Y.

[21] Appl. No.: 390,098

[22] Filed: Jun. 21, 1982

[51] Int. Cl.³ ............................................. G01N 33/28
[52] U.S. Cl. ..................................................... 73/60.1
[58] Field of Search ................................ 73/60.1, 61.3

[56] References Cited

U.S. PATENT DOCUMENTS 3,151,061  9/1964  Orr .................................... 73/60.1 X

FOREIGN PATENT DOCUMENTS 735795  4/1943  Fed. Rep. of Germany ....... 73/60.1
277397  10/1970  U.S.S.R. ................................ 73/60.1
415554  7/1974  U.S.S.R. ................................ 73/60.1

Primary Examiner—Gerald Goldberg
Assistant Examiner—Joseph W. Roskos
Attorney, Agent, or Firm—Alexander J. McKillop; James F. Powers, Jr.; Lawrence O. Miller

[57] ABSTRACT

Measuring the foaming characteristics of crude oil comprises saturating the crude oil with a gas inert to the crude oil under high pressure and passing the gas-saturated oil into a flash separator. The amount of foam formed is measured with respect to the amount of gas withdrawn from the flash separator and the amount of oil contained therein. The apparatus comprises a gas-oil saturation vessel, a transparent elongated horizontal flash separator, an oil inlet line in one end of the flash separator, an oil outlet line in the bottom portion of the flash separator at the end opposite the oil inlet, a gas outlet line in the upper portion of the flash separator between the oil inlet and oil outlet line, a pressure equalization line in communication with the upper portion of the flash separator, the gas outlet line, and the oil outlet line, a weir for maintaining a layer of oil in the lower portion of the flash separator at a controlled level, a transverse baffle extending from the upper portion of the flash separator to a point below the height of the weir, located near the weir and upstream thereof, means for measuring the oil flow rate from the flash separator, means for measuring the gas flow rate from the flash separator, means for controlling the back pressure within the flash separator, means for controlling the temperature in the gas-oil saturator and the flash separator, and means for measuring the foam volume in the flash separator.

9 Claims, 6 Drawing Figures

METHOD AND APPARATUS FOR DETERMINING THE FOAMING CHARACTERISTICS OF CRUDE OIL

FIELD AND BACKGROUND OF THE INVENTION

1. Field of the Invention

The invention relates to a method and apparatus for determining the foaming characteristics of crude oil.

2. Background of the Invention

The foaming characteristics of crude oil streams produced from a well are important in designing apparatus for separating the crude oil stream into oil and gas. The most common method of separating oil and gas produced from a well is to pass the oil and gas mixture under an initial high pressure into a vessel under reduced pressure wherein the gases dissolved in the oil flash off the oil and the heavier oil separates from the gas by gravity. The volume of the vessel and the retention time of the oil are sufficient to allow the oil to accumulate and to be withdrawn from the bottom portion of the vessel with the separated gas being withdrawn from the top portion of the vessel. As gas separates from the oil, foam accumulates on the top of the oil and the amount of foam formed will vary depending upon the characteristics of the crude oil being produced. Therefore, the capacity of the vessel must be sufficient to accommodate the volume of foam formed in the vessel based upon the foaming characteristics of the crude oil and crude oil production.

Presently, the foaming characteristics of oil are measured by bubbling a gas through a sparger tip into a given volume of oil, contained in some suitable measuring vessel. This practice is unsatisfactory because the character of the sparger tip may change over a period of usage and resulting foams are not properly comparable. Furthermore, the bubbles of foam formed with sparger systems are usually larger than those which result from the self-nucleation of foam by decreasing the pressure on a gas-saturated liquid, i.e., when the gas is "flashed" from the liquid.

The present invention provides an improved method for measuring the foaming characteristics of crude oil utilizing a gas-oil saturator and a flash separator comprising a transparent elongated horizontal cylinder.

SUMMARY

The present invention relates to a method for measuring the foaming characteristics of oil comprising saturating a predetermined volume of oil with a gas inert with the oil at a predetermined pressure and temperature, introducing the oil saturated with gas at a predetermined rate into one end of an elongated horizontal transparent flash separator at a predetermined pressure substantially lower than the gas-oil saturation pressure so that the gas saturated oil upon exposure to the reduced pressure separates into a gaseous portion that passes to the upper portion of the separator, a body of oil that extends along the bottom of the flash separator and a layer of foam that accumulates on the top of the oil, controlling the temperature of the oil in the flash separator to a temperature equal to the gas saturation temperature, withdrawing gas from the upper portion of the flash separator near the end opposite the oil inlet and measuring the gas flow rate, withdrawing oil from the bottom portion of the flash separator near the end opposite the oil inlet and measuring the oil flow rate, controlling the level of oil in the separator by means of a weir extending from the bottom portion of the separator located between the oil inlet and the oil outlet of the separator, preventing the layer of foam accumulating on the top of the oil from passing beyond the weir by means of a transverse baffle extending from the top of the separator, and determining the foam volume within the flash separator.

In accordance with another aspect of the invention, there is provided an apparatus for measuring the foaming characteristics of an oil comprising a gas-oil saturation vessel, means for supplying a gas under pressure to the gas-oil saturation vessel, means for supplying a predetermined volume of an oil sample to the gas-oil saturation vessel, means for controlling the temperature of the gas-oil saturation vessel, a flash separator comprising an elongated horizontal transparent vessel, an oil inlet line located in one end of the flash separator, conduit means for connecting the gas-oil saturation vessel to the oil inlet line of the flash separator, an oil outlet line located in the bottom portion of the flash separator near the end of the flash separator opposite the oil inlet, a gas outlet line located in the upper portion of the flash separator between the oil inlet line and the oil outlet line of the flash separator, into a portion of the cross-sectional area of the flash separator located between said gas outlet line and the oil outlet line of the flash separator, a weir extending from the bottom portion of the flash separator located between the gas outlet line and the oil outlet line of the flash separator, a transverse baffle extending from the upper portion of the flash separator to a point below the height of the weir located between the gas outlet line and the weir, back pressure control means in the gas outlet line for maintaining a pressure in the flash separator substantially less than the gas-oil saturation pressure, means for controlling the temperature of the flash separator, means for measuring the gas flow rate from the flash separator, means for measuring the oil flow rate from the flash separator, and means for measuring the foam volume within the flash separator.

DESCRIPTION OF THE PREFERRED EMBODIMENT

Figure 1:
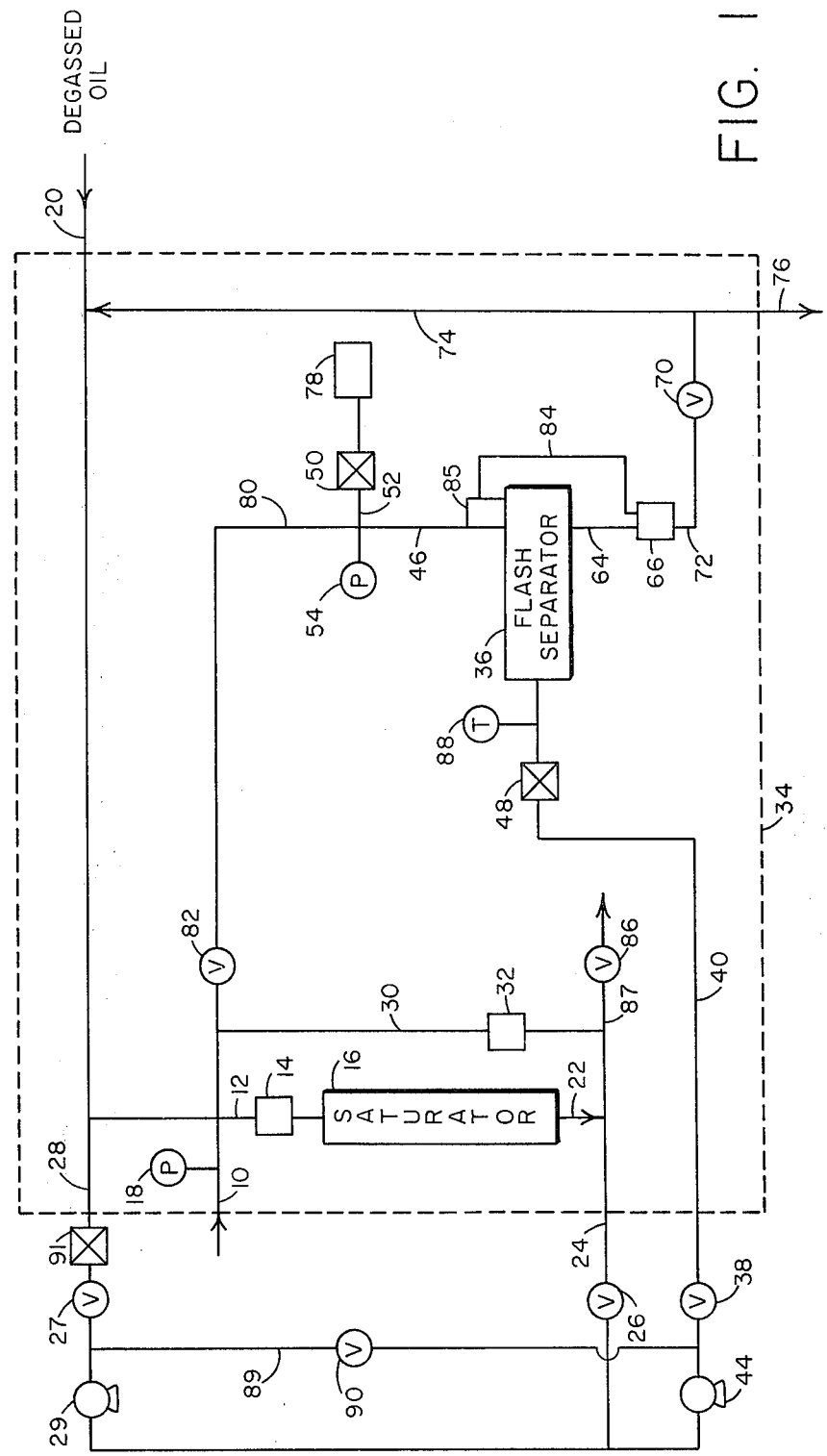
FIG. 1 is a diagrammatic representation of the apparatus for measuring the foaming characteristics of crude oil in accordance with this invention and adapted to carry out the method thereof.

Referring to FIG. 1, methane gas from a suitable source (not shown) is introduced via line 10, line 12 and sight glass 14 into a gas-oil saturator 16 under a high pressure as measured by pressure gauge 18. In a specific example, gas-saturator 16 is a one-liter steel cylinder rated for high pressure operation and mounted vertically. Saturation pressures may vary within the range of 50 and 1000 psi. A predetermined amount of crude oil to be tested for foaming characteristics is introduced into the gas-oil saturator 16 under pressure via line 20 connected to line 12 and sight glass 14. The sight glass 14 is partially filled with ceramic packing material to provide additional surface for the test crude oil to be intimately contacted by methane. Additional ceramic packing is located below the sight glass in an inlet fitting that connects the sight glass to the gas-oil saturator 16. Although methane is the preferred saturating gas, other gases which are inert to the oil being tested may be used such as ethane, propane, nitrogen and carbon dioxide.

An outlet line 22 is located at the bottom of the gas-oil saturator 16 for withdrawing the gas-saturated oil from the saturator. Oil withdrawn from the gas-oil saturator 16 via line 22 is recirculated to inlet line 12 of the separator via line 24, valves 26, and 27, and flow line 28 by means of pump 29 to enable the oil to come into repeated contact with methane gas to assure complete saturation thereof. Line 30 is connected to the inlet line 12 and outlet line 22 of the gas-oil saturator so as to allow pressure to equilibrate above and below the gas-oil saturator during pumping operations. A high pressure sight glass 32 parallel to the gas-oil saturator 16 is located in the lower half of pressure equalizing line 30 to allow observation of the oil level in the gas-oil saturator. The top edge of the sight glass window is level with the middle of the gas-oil saturator 16 so that the gas-oil saturator is at least half full when the sight glass is full of oil.

Gas-saturation of the oil in gas-saturator 16 is conducted at a predetermined temperature by placing the saturator including all connecting elements within an insulated housing 34 heated by suitable means as described hereinafter.

Once the crude oil is saturated with methane under a fixed high pressure and temperature, the gas-saturated oil is delivered to flash separator 36 via valve 26 in line 24 and valve 38 in flow line 40 by means of pump 44. Flash separator 36 comprises an elongated horizontal transparent cylindrical vessel closed at both ends with a suitable gas outlet line 46 provided in the upper portion of the separator in the end of the separator opposite from the oil inlet end. A back pressure regulator 48, which may be of conventional design, is connected in line 40 to control the pressure of the gas-saturated oil prior to entering the separator 36 at a pressure equal to or greater than the gas-oil saturation pressure so as to prevent foaming of the oil upstream of the separator.

The gas-saturated oil undergoes a sharp pressure drop in flash separator 36. Pressure in the flash separator 36 is controlled by a back pressure regulator 50 in branch line 52 connected to gas outlet line 46. The pressure in flash separator 36 is measured by pressure gauge 54 connected to gas outlet line 46. Back pressure regulator 50 maintains a given pressure in the separator 36 so that effects of pressure on foaminess may be observed and to enable variations in the gas evolution rate in the separator.

Figure 2:
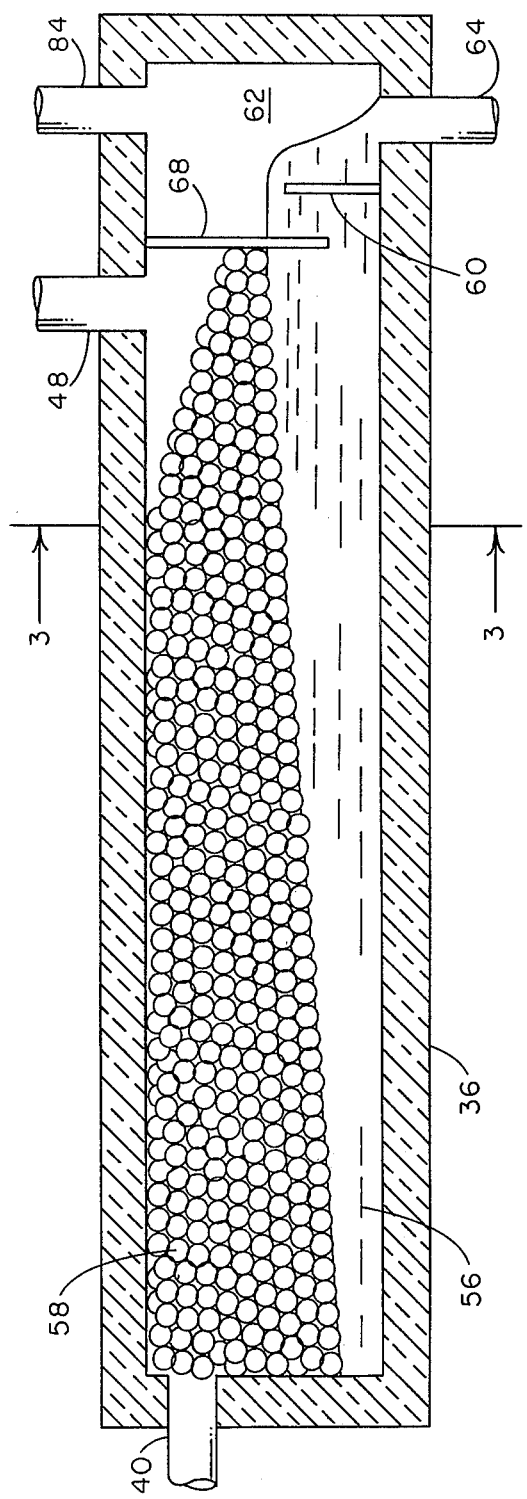
FIG. 2 is a longitudinal, vertical, cross-sectional view of a flash separator as employed in the system of FIG. 1.
Figure 3:
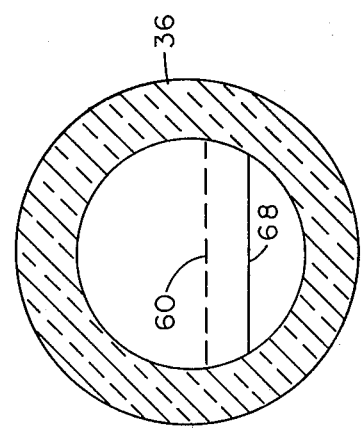
FIG. 3 is a sectional view taken along line 3—3 of FIG. 2.

In a specific example, as shown in FIG. 2, flash separator 36 is preferably machined from a 1½ inch ID Plexiglass tube having a ¼ inch wall thickness and 8 inch length with markings affixed to the outside surface of the Plexiglass cylinder for visually measuring the height of the oil and foam with the flash separator. The transparent Plexiglass tube enables the foaming conditions to be visually observed. The gas-saturated oil enters flash separator 36 through line 40 and due to the sharp decrease in pressure within the separator, the oil resolves into a gaseous phase that rises to the upper portion of the separator, a body of oil 56 that separates to the bottom portion of the separator, and a layer of foam 58 that accumulates on top of the oil 56, see FIG. 2. Referring to FIG. 2, the flash separator is provided with a weir 60 extending from the bottom of the separator into a portion of the cross-sectional area of the separator located in the end of the separator opposite from the oil inlet 40 to control the level of the oil. Oil passing over weir 60 flows into a sump 62 and is withdrawn from the separator 36 through an oil outlet line 64 and delivered to oil trap 66 (see FIG. 1). Flash separator 36 is also provided with a transverse baffle 68 located near weir 60 and upstream thereof to prevent foam from passing over the weir into sump 64 thereby enabling complete separation of the oil from the foam. In addition, baffle 68 confines the layer of foam 58 within a fixed horizontal distance so as to permit foam volume measurements to be made visually as described in detail below. As shown in FIG. 3, baffle 68 extends below the oil level provided by weir 60 so that oil passes under the baffle, over weir 60 and into sump 62 for removal through oil outlet line 64. The oil trap 66, shown in FIG. 1, is transparent and graduated on the outside surface with a suitable scale so that volumetric measurements of the oil within the oil trap can be made. In a specific example, oil trap 66 is machined from a 1½ inch ID Plexiglass tube with ¼ inch wall.

Oil in oil trap 66 may be withdrawn via line 72 and valve 70 and either be recycled to the gas-oil saturator 16 via line 74 or delivered into a waste container (not shown) via line 76. Methane that flashes from the oil in flash separator 36 is withdrawn from the separator through line 46 and branch line 52 and delivered to a gas flow measuring apparatus 78. Pressure equalization lines 84 and 85 are connected to sump 62 in the flash separator 36 and to the top of oil trap 66 and gas outlet line 46 to allow pressure to equalize as oil flows out of separator 36 and fills the oil trap 66.

Whenever the gas-oil saturator 16 becomes overpressurized with methane, the excess pressure can be bled off to flash separator 36 via valve 82 in flow line 80. Also, when foam tests at higher separator pressures are desired, methane from the saturator 16 may be used to pressurize the flash separator 36 via line 80. The advantage of adding pressurized methane to the flash separator in this fashion is to prevent severe foaming which occurs if the oil is introduced into a depressurized separator.

Flow line 89 connecting the outlet line of pump 29 to the outlet line of pump 44 allows the combined flow of pump 29 and pump 44 to be recirculated in the saturator or to be diverted to the separator. Any pressure differential between flow line 28 and flow line 40 may be equilibrated by opening valve 90 in flow line 89.

The back pressure regulator 91 is adjusted to provide a small head of pressure between the outlet and inlet lines of the circulating pumps to help seat the pump seals.

During cleaning operations, oil may be withdrawn from the bottom of gas-oil saturator 16 via line 87 and valve 86 connected to line 22, see FIG. 1.

As in the case of the gas-saturator 16, the flash separator 36 including all connecting elements are placed within an insulated housing 34 heated by suitable means to maintain the entire assembly except for pumps at a predetermined temperature. In a specific example, temperature control may be maintained by placing the entire assembly in a Shel-Lab Incubator, Model 22, fitted with a glass door, manufactured by Sheldon Manufacturing, Inc., Aloha, Oreg.

Referring to FIG. 1, foam temperature is monitored at the inlet of flash separator 36 by means of a sensing element 88 comprising a digital thermometer with a copper-constantan thermocouple, Analogic Model 2572, manufactured by Analogic Corporation, Wakefield, Mass.

OPERATION

The operating procedure employed in this invention comprises delivering high pressure methane into gas-oil saturator 16 through line 10, line 12 and sight glass 14 at the desired gas-oil saturation pressure which for example is 300 psig. One liter of crude oil to be tested for foaminess is pumped into the gas-saturator 16 via line 20.

Before introduction of methane into gas-saturator 16 three operations must be performed.

1. Valves 38, 82, and 86 are closed.
2. Sufficient oil is added to the system to allow the circulating pumps to operate without entrapment of air bubbles.
3. Back pressure regulators 48 and 91 are adjusted to 35 psi above the saturator pressure.

One liter of crude oil to be tested for foaminess is pumped into the gas-saturator 16 via line 20. Methane is introduced via line 10. The pressure of back pressure regulators 48 and 91 and the methane pressure are alternately increased by 50 psi increments while assuring that the pressure of the back pressure regulators remains at least 35 psi above the methane pressure. When the desired pressure is attained valve 38 may be cracked open to allow oil to fill line 40. Valve 38 must be opened slowly to prevent a pressure surge from damaging the pump seals. The methane and oil are heated to a specified temperature by confining the gas-saturator 16 and connecting elements within an insulated housing 34 heated by suitable means. At this point, to thoroughly commingle oil and gas so as to increase gas saturation efficiency, oil is withdrawn from the gas-oil saturator 16 via line 22 and recirculated to the saturator by means of pump 29 via lines 24 and 28. Complete gas saturation of the oil is determined by stopping the flow of methane and observing any pressure drop by means of pressure guage 18 which will occur if methane is still being dissolved in the oil. When no pressure drop is observed, the maximum amount of methane has dissolved in the oil and, therefore, gas saturation of the oil is complete.

The gas saturated crude oil may be pumped safely into flash separator 36 since the inlet back pressure regulator 48 is adjusted to a pressure at least 35 psig above the gas-oil saturator pressure to prevent oil, gas and foam from being violently blown into the flash separator 36. Without the 35 psig pressure differential, oil will flash in the pump lines prior to entering the flash separator 36. Back pressure regulator 50 located in gas outlet line 46 must also be adjusted whenever separator pressure above atmospheric pressure are desired.

Coarse flash separator pressure adjustments are made by increasing the pressure on back pressure regulators 48 and 50 and allowing small amounts of methane to enter flash separator 36 via line 80. Fine adjustments are made during actual foam tests by increasing or decreasing the gas pressure on back pressure regulators 48 and 50 while gas escapes from the foam.

Foam tests are initiated by delivering gas-saturated oil to the flash separator 36 by means of pump 44 via line 40. The pressure within flash separator 36 is maintained at a reduced pressure by back pressure regulator 50 connected to gas outlet line 46 which by way of example is 10 psig. Once the gas-saturated oil enters flash separator 36 under reduced pressure, methane separates from the oil and passes upwardly into the top portion of the separator. The separated oil and foam pass downwardly by gravity into the bottom of the flash separator 36 forming a body of oil 56 extending along the entire length of the separator and the lighter foam accumulates in a layer 58 on top of the body of oil, see FIG. 2. The separated oil passes under baffle 68 and over weir 60 into sump 62 and is withdrawn from separator 36 via line 64 into oil trap 66. Oil trap is transparent and has volumetric markings affixed on the outside surface to measure the amount of oil therein. When the foam volume reaches steady state, usually the time required for oil to reach the height of 1 cm in oil trap 66, foam height measurements are visually recorded by means of a linear scale on the outside wall of flash separator 36. The time required for oil to fill the oil trap 66 between two specified markings is recorded. After the timer has been reset, the time required for gas to fill gas measuring apparatus 78 to a specified volume via line 52 is recorded. The gas measuring apparatus 78 comprises a gas holder consisting of a modified graduated cylinder immersed in and filled with water. As gas fills the holder, the holder is raised to keep the water within and outside the holder at the same level. By maintaining a constant water level as the gas volume increases, the holder pressure remains at atmospheric pressure. After gas flow rate measurements have been completed, the gas-saturated oil flowing into the flash separator 36 via line 40 is diverted to line 28 by opening valve 90 and closing valve 38 so as to recirculate oil into gas-saturator 16. Foam temperature is monitored by temperature measuring device 88. When desired, the oil in oil trap 66 may be withdrawn through line 72 and either returned to the gas-saturator 16 via line 74 or it may be discarded through line 76.

Figure 4A:
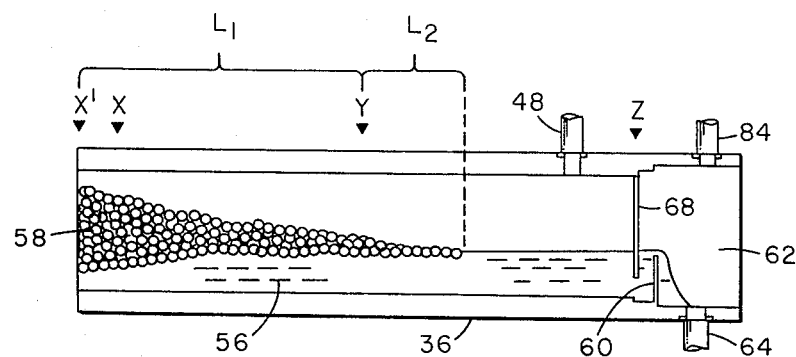
FIGS. 4a, 4b, and 4c are longitudinal, vertical, cross-sectional views of the flash separator as employed in the system of FIG. 1 illustrating various stages of foam formation in the flash separator.
Figure 4B:
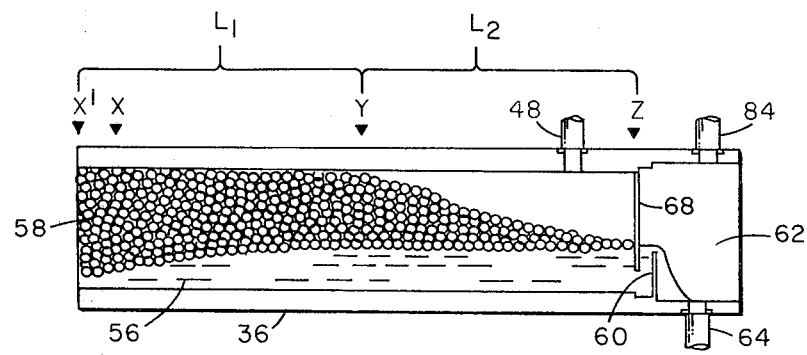
Figure 4C:
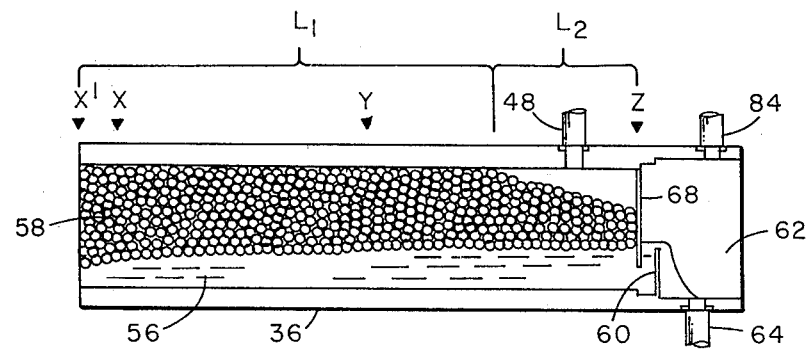

FIGS. 4a, 4b, and 4c illustrate foam conditions at various stages of the present method including the technique used to measure foam wedge volume on the top of the oil. Foam wedge volumes are difficult to measure accurately in transparent horizontal cylinders due to parallax problems, optical distortions, and nonlinear meniscus formations. Parallax problems are diminished by taking readings perpendicular to the foam and oil heights. Since readings are taken from length markings on tape affixed to the outside surface of the cylinder, the measurements must be converted from external circumference measurements to internal foam and oil heights. From a table of circular segments the height measurements are converted to the respective oil and foam-plus-oil cross sectional areas. Since the foam height measurement is the height of the foam above the bottom of the separator, the oil height is included in that value. Foam area is calculated by subtracting the oil cross sectional area from the foam-plus-oil cross sectional area. Inlet cross sectional areas are derived using the inlet height values extrapolated from the heights measured on the x and y scales. A linear relationship is assumed to exist between the x and y measurements.

EXAMPLE

A typical foam volume measurement where foam test conditions are 10 psig separator pressure, 300 psig saturator pressure, and temperature maintained between 126° to 121° F. (the temperature of the flashing oil at the start and end of the foam measurements) is conducted as follows:

The oil flow rate timer was started when the oil level in the separator oil trap 66 reached the 1 cm mark. Next, the foam heights were measured on the external x, y, and z scales to be 2.9 to 3.2 cm (average=3.05), 2.3 to 2.4 cm (average=2.35), and 1.0 cm, respectively, as shown in FIG. 4a. The z scale reading of 1.0 cm suggests that the foam subsides to the oil level which is maintained at the 1.0 cm mark. Although no foam was actually present at the z scale location, 1 cm was recorded as a reminder that the foam has subsided to the oil surface and that the location where the foam breaks the oil surface was recorded, in this case 1.5 to 1.0 cm from the z scale. In a similar fashion the oil heights were measured to be 1 cm on each scale. The dual foam height measurements on the x and y scales and the dual subsidence point measurements are indicatiave of unstable foam volumes which do not reach a steady state and fluctuate between two volumes.

Measurements in the separator vessel 36 were concluded when the oil flow rate time was stopped at 2.34 minutes as the oil level in the separator oil trap 66 reached the 7 cm mark.

Gas flow rate measurements were taken outside the separator 36 in gas collecting vessel 78 at ambient temperature and pressure, 74° F. and 744 mm Hg. Methane gas, 300 ml, was collected in 0.74 minute and vented out of the laboratory with any residual methane gas flowing out of the separator.

Since two values were recorded for the foam height on the x and y scales, the average foam heights (3.05 and 2.35 cm, respectively) were used in the foam volume calculations. Averaging was used in all cases where measurements fluctuated between two points. The conversion of external tape measurements to internal foam height values of 3.05, 2.45 and 1.43 for x, y, and z was accomplished through the use of a graph generated from equations correlating circle radius to circumference. Math tables were used to convert the height measurements to cross-sectional areas of 9.205, 7.730, and 3.891 $cm^2$. Oil cross-sectional areas were found in a like manner to be 3.891 $cm^2$, which is a constant value at the weir plate 60, see FIG. 2.

Before volume calculations could be made, the cross-sectional areas of foam and oil at the inlet of the separator vessel were required. Given the distance of the x scale to be 1.44 cm from the inlet and the y scale to be 8.68 cm from the inlet and assuming a linear relationship to exist between the x and y height measurements, the straight line equation can be employed to extrapolate the inlet height value. The foam and oil heights at the inlet were found to be 3.17 cm and 1.43 cm, respectively, and the inlet cross-sectional areas, 10.138 $cm^2$ and 3.891 $cm^2$, were found using the same techniques as in the derivation of the x, y and z areas. The cross-sectional areas derived from the foam height measurements are the summation of the foam and oil cross-sectional areas. To calculate foam volume using cross-sectional areas derived from the foam height measurements, the oil cross-sectional area must be subtracted.

The foam volume equation and the oil volume equation are given below.

$$V_F = \frac{L_1}{2}[(A_{F+O} - A_O)_{x'} + (A_{F+O} - A_O)_y] +$$

$$\frac{L_2}{2}[(A_{F+O} - A_O)_y + (A_{F+O} - A_O)_z]$$

$$V_O = \frac{L_1}{2}[A_O + A_O]_{x'\ y} + \frac{L_2}{2}[A_O + A_O]_{y\ z} + 2.2\ ml$$

where $V_F$ is foam volume, $V_O$ is oil volume, $A_{F+O}$ and $A_O$ are the calculated cross-sectional areas derived from the foam plus oil and the oil height measurements obtained at the x, y, and z scales; x' represents the foam-plus-oil and the oil heights extrapolated to the inlet; and $L_1$ and $L_2$ are distances between these cross-sectional areas, usually 8.68 and 8.47 cm, respectively—the distance between the inlet and the y scale and the distance between the y and the z scales (FIG. 4b). If the foam subsides to the oil level before reaching the y or z scales, the $L_1$ and $L_2$ values must be adjusted accordingly (FIG. 4a). Where the foam subsides after reaching the y scale $L_1$ must be adjusted (FIG. 4c). In these experiments, it was convenient to measure horizontal distances beginning at the baffle plate; so the data book shows zero distance at the baffle. The 2.2 ml value is the volume of oil that remains beneath and between the baffle and weir.

Given the values obtained during the flash separator experiment, the foam volume equation may be written as follows:

$$V_F = \frac{8.68}{2}[(10.138 - 3.891)] +$$

$$\frac{7.22}{2}[(7.730 - 3.891) + (3.891 - 3.891)]$$

$$V_F = 57.6\ cm^3$$

Here, the foam subsided to the oil level at the horizontal distance of 1.25 cm from the z scale making $L_2$ equal to 7.22 cm.

The oil volume was calculated as follows:

$$V_O = (17.15 \times 3.891) + 2.2$$

$$V_O = 68.9\ cm^3$$

Since the oil level remained constant in the example given, 3.891, the cross-sectional area of the oil, is a constant and the oil volume equation reduces to the sum of the product of the vessel length 17.15 and the oil cross-sectional area 3.891, and 2.2.

Conversion of gas volume measurements to gas flow rates through the separator, $Q_G$, at temperature and pressure is provided by Equation 1.

$$Q_G = \frac{V_g}{t_g} \frac{p_a}{p_s} \frac{T_s}{T_a} \qquad (1)$$

where $T_s$ is the separator temperature in °R (460+T°F.=°R); $p_s$ is the separator pressure in psia (psig+14.7=psia); $p_a$ is the ambient pressure in psia; $V_g$ is the measured gas volume; $t_g$ is the time elapsed during gas volume measurement; and $T_a$ is the room temperature in °R. Substitution of the gas flow rate data into Equation (1) yields:

$$Q_G = \frac{300 \text{ ml}}{0.74 \text{ min}} \times \frac{14.39 \text{ psia}}{24.7 \text{ psia}} \times \frac{583.5° \text{ R.}}{534° \text{ R.}}$$

$$Q_C = 258.09 \text{ ml/min}$$

The oil flow rate through the separator, $Q_O$, is given by Equation 2:

$$Q_O = \frac{1}{t_O} (11.4)(h_O) \quad (2)$$

where 11.4 cm² is the cross-sectional area of the oil trap, $h_O$ is the distance in cm the oil level rises during the time interval, $t_O$. For the example given the equation becomes:

$$Q_O = \frac{11.4 \text{ cm}^2 \times 6 \text{ cm}}{2.34 \text{ min}}$$

$$Q_O = 29.23 \frac{\text{cm}^3}{\text{min}}$$

The foam volume to oil volume ratio is now easily calculated and converted to field units:

$$\frac{V_F}{V_1} = \frac{57.6 \text{ cm}^3}{68.9 \text{ cm}^3} \times \frac{\frac{1 \text{ ft}^3}{28,316 \text{ cm}^3}}{\frac{1 \text{ BBL}}{158,980 \text{ ml}}}$$

$$\frac{V_F}{V_1} = 3.728 \text{ ft}^3/\text{BBL}$$

where $V_1$ is the volume of oil initially in the separator. The actual gas evolution rate AGER is calculated and converted to field units in the following manner:

$$AGER = \frac{Q_G}{V_1} = \frac{258.09 \text{ ml/min}}{68.9 \text{ ml}} \times \frac{\frac{1 \text{ ft}^3}{28,316 \text{ ml}}}{\frac{1 \text{ BBL}}{158,980 \text{ ml}}}$$

$$AGER = 21.01 \text{ ACF/BBL/min}$$

Thus, there have been described specific embodiments for determining the foaming characteristics of a crude oil by reducing the pressure on a gas-saturated crude oil. It will be understood by those skilled in the art that the above-described embodiments are merely exemplary and that they are susceptible to modification and variation without departing from the spirit and scope of the invention.

What is claimed is:

1. A method for measuring the foaming characteristics of oil comprising:
   (a) saturating a predetermined volume of oil with a gas inert with the oil at a predetermined pressure and temperature;
   (b) introducing said gas-saturated oil at a predetermined rate into one end of a flash separator comprising an elongated horizontal transparent vessel, said flash separator maintained at a predetermined pressure substantially lower than the gas saturation pressure so that the gas saturated oil upon exposure to the reduced pressure separates into a gaseous portion that passes to the upper portion of the separator, a body of oil that extends along the bottom of the separator and a layer of foam that accumulates on top of the oil;
   (c) controlling the temperature of the flash separator at a temperature equal to the gas saturation pressure;
   (d) withdrawing gas from the upper portion of the flash separator near the end opposite the oil inlet and measuring the gas flow rate;
   (e) withdrawing oil from the bottom portion of the flash separator near the end opposite the oil inlet and measuring the oil flow rate;
   (f) maintaining a layer of oil in the lower portion of the flash separator at a controlled level by means of a weir extending from the bottom of the separator located between the oil inlet and the oil outlet of the separator;
   (g) preventing the layer of foam accumulating on the top of the oil from passing beyond said weir by means of a transverse baffle extending from the top of the separator; and
   (h) determining the foam volume within the flash separator.

2. The method of claim 1 wherein the saturating gas is methane.

3. The method of claim 1 wherein the saturating gas is selected from the group consisting of methane, ethane, propane, carbon dioxide, and nitrogen.

4. The method of claim 1 wherein the gas saturation pressure is within the range of 50 and 1000 psi, the flash separator pressure is within the range of 0 and 100 psi, and the gas saturation temperature and flash separator temperatures are within the range of 50° and 200° F.

5. The method of claim 1 wherein the gas saturation pressure is 300 psig, the flash separator pressure is 10 psig, and the gas saturation temperature and flash separator temperature is 126° F.

6. Apparatus for measuring the foaming characteristics of an oil comprising:
   (a) a gas-oil saturation vessel;
   (b) means for supplying a gas under pressure to said gas-oil saturation vessel;
   (c) means for supplying a predetermined volume of said oil sample to said gas-oil saturation vessel;
   (d) means for controlling the temperature of said gas-oil saturation vessel;
   (e) a flash separator comprising a transparent elongated horizontal vessel;
   (f) an oil inlet line located in one end of said flash separator;
   (g) conduit means for connecting the gas-oil saturation vessel to the oil inlet line of flash the separator;
   (h) an oil outlet line located in the bottom portion of the flash separator near the end of the flash separator opposite the oil inlet;
   (i) a gas outlet line located in the upper portion of the flash separator between the oil inlet line and the oil outlet line;
   (j) a pressure equalization line in communication with the upper portion of the flash separator, the gas outlet line, and the oil outlet line;
   (k) a weir extending from the bottom of the flash separator into a portion of the cross-sectional area of the flash separator located between the gas outlet line and the oil outlet line of the flash separator;
   (l) a transverse baffle extending from the upper portion of the flash separator to a point below the height of said weir located between said gas outlet line and said weir;

(m) back pressure control means in the gas outlet line for maintaining a pressure in the separator substantially less than the oil saturation pressure;

(n) means for controlling the temperature of the flash separator;

(o) means for measuring the gas flow rate from the flash separator;

(p) means for measuring the oil flow rate from the flash separator;

(q) means for measuring the foam volume in the flash separator.

7. The apparatus of claim 6 further comprising back pressure control means in the conduit connecting the gas-oil saturator and the flash separator located near the inlet to the flash separator so as to maintain gas-oil saturation pressure in said conduit.

8. The apparatus of claim 6 wherein the flash separator comprises an elongated horizontal Plexiglass cylinder with markings affixed to the outside surface of the Plexiglass cylinder for measuring the height of the foam and oil within the flash separator.

9. The apparatus of claim 6 wherein the gas-oil saturator comprises a steel cylinder.

* * * * *